(12) United States Patent
Tellier et al.

(10) Patent No.: US 6,190,646 B1
(45) Date of Patent: Feb. 20, 2001

(54) NUTRIENT MICROEMULSION IN SPRAY FORM, USEFUL AS A BIODEGRADATION ACCELERATOR

(75) Inventors: Jacques Tellier, Lons; Anne Basseres, Bizanos; Pascal Brochette, La Gacilly; Alexandre Espert, Pau, all of (FR)

(73) Assignee: Elf Aquitaine, Courbevoie (FR)

( * ) Notice: Under 35 U.S.C. 154(b), the term of this patent shall be extended for 0 days.

(21) Appl. No.: 09/395,974

(22) Filed: Sep. 15, 1999

(30) Foreign Application Priority Data

Jul. 6, 1999 (FR) ..................................... 9908678

(51) Int. Cl.$^7$ ................ A61K 7/08; A61K 7/09; A61K 7/075
(52) U.S. Cl. .................... 424/70.19; 424/70.21; 424/70.22; 424/70.27; 424/70.31
(58) Field of Search .............. 424/70.19, 70.21, 424/70.22, 70.27, 70.31

(56) References Cited

U.S. PATENT DOCUMENTS 5,236,615 * 8/1993 Trinh et al. ..................... 252/174.11
5,869,442 * 2/1999 Srinivas et al. ..................... 510/476

* cited by examiner

*Primary Examiner*—David M. Naff
*Assistant Examiner*—Deborah K. Ware
(74) *Attorney, Agent, or Firm*—Oblon, Spivak, McClelland, Maier & Neustadt, P.C.

(57) ABSTRACT

A microemulsion is prepared containing: a mixture of (1) nitrogenous compounds, (2) from 10–5% by weight of an alkyl or alkenyl phosphoric ester surfactant, the alkyl and alkenyl groups of which contain less than 12 carbon atoms per group and the ester surfactant containing from 1 to 10 alkoxy radicals, (3) from 3 to 20% by weight of at least one cosurfactant, (4) a vegetable oil, an animal oil or a fatty acid and (5) a plasticizer. The microemulsion having a viscosity at 5° C. less than or equal to 200 mPa·sec and is stable at a temperature of −10° C. to +50° C. Further, the microemulsion is useful as a biodegradation accelerator.

19 Claims, No Drawings

NUTRIENT MICROEMULSION IN SPRAY FORM, USEFUL AS A BIODEGRADATION ACCELERATOR

BACKGROUND OF THE INVENTION

1. Field of the Invention

The present invention relates to a biodegradation accelerator of hydrophobic pollutants such as hydrocarbons, of oil/water microemulsions, also called nutrient microemulsions, which are consumable by microorganisms.

2. Description of the Related Art

The formulation of the nutrient microemulsions in the past has represented a significant advance in the marketing of additives which are useful as biodegradation accelerators. For example, French Patent Nos. 2,490,672 and 2,512,057 describe such accelerators, which are formulated as an internal phase of an aqueous solution of nitrogenous and phosphorus compounds, preferably phosphorous surfactants, this phase being dispersed in an external hydrophobic phase formed of an easily assimilated carbon source. In these emulsions, the nitrogenous compounds employed are, for example, amino acids, proteins, or urea, and phosphorous compounds of surfactants of the alkyl or alkenyl phosphoric ester type. The hydrophobic external phase is formed of a carbon source easily assimilated by microorganisms, such as vegetable oils or, animal oils and fatty acids, which are selected in order to be compatible with the products to be degraded.

The effectiveness of these known emulsions as biodegradation accelerators has been clearly demonstrated in numerous industrial applications, especially in the treatment of effects of marine pollution resulting from accidental spills of hydrocarbons and in the treatment procedures which are directed to the rehabilitation of soil contaminated with hydrophobic pollutants such as described in patent WO 95/06715.

Despite the qualities of nutrient microemulsions, their use remains limited on account of difficulty in use, in particular at temperatures below 10° C.

The microemulsions described in the state of the art are generally applied in spray form to the contaminated zones or mixed with polluted soil. They must therefore exhibit certain fluidity and a certain stability favoring such applications. Yet, these microemulsions have the disadvantage of separating into two immiscible phases near 0° C. In addition, whenever an ambient temperature lower than 20° C. is reached, these microemulsions become very viscous (more than 1,000 mPa·sec), which makes their use on the soil very tricky or even impossible in certain forms of application such as by a spray.

Of course, attempts have been made to remedy this major drawback by the addition of organic compounds, such as alcohols and glycol ethers, to decrease the viscosity of these microemulsions at these temperatures, as is mentioned in application WO 9/07508. Thus, by adding from 10 to 15% ethylene glycol butyl ether, a decrease in the viscosity to approximately 200 mPa·sec at 20° C. has been observed, allowing spraying of the product with conventional equipment at this temperature, or an easier spreading. However, to apply these microemulsions at a lower temperature, in particular below 10° C., it is currently advisable either to store the microemulsions at 20° C. in order to spray the microemulsions at this temperature, or to reheat the microemulsions on site while the microemulsions are reformed and/or become fluid again. It is a major drawback for the user who, as the product is transformed, is no longer certain of the quality of his product. Therefore, it is understood why the use of this biodegradation accelerator, otherwise remarkable in its effectiveness, has not been widely extended to all applications for marine or terrestrial biodegradation, in particular, in cold countries.

SUMMARY OF THE INVENTION

Accordingly, one object of the present invention is to provide a microemulsion which is useful as a biodegradation accelerator which is nontoxic, which is stable at temperatures from −10° C. to +50° C., and which has a fluidity at +5° C. which is sufficient for use in the applications desired.

Briefly, this object and other object of the present invention as hereinafter will become more readily apparent can be attained by a microemulsion which is useful as a biodegradation accelerator, the microemulsion containing (1) at least one nitrogenous compound such as amino acids, proteins, urea and its derivatives, (2) from 10 to 35% by weight of a phosphorus surfactant compound of the alkyl or alkenyl phosphoric ester type, the ester being a mono- and/or dialkyl- or mono- and/or dialkenylphosphoric ester wherein the alkyl and alkenyl groups contain less than 12 carbon atoms per alkyl or alkenyl chain, preferably from 3 to 10 carbon atoms and containing from 1 to 10 alkoxylated radicals, preferably ethoxy and/or propoxy groups, (3) from 3 to 20% by weight of at least one cosurfactant, (4) a compound selected from the group consisting of vegetable oils, animal oils and fatty acids, and (5) a plasticizer, said emulsion having a viscosity at 5° C. less than or equal to 200 mPa·sec and stable at a temperature of −10° to +50° C.

DETAILED DESCRIPTION OF THE PREFERRED EMBODIMENTS

In the present invention, it is the combined effect of the surfactants derived from the above specific phosphoric esters, with a cosurfactant or a mixture of cosurfactants, which assures the stability of the microemulsion down to a very low temperature, at least −10° C., and allows the product to be used without difficulty in any cold environment.

The cosurfactants according to the invention are selected from compounds with an oral toxicity in rats, such that the lethal dose for 50% of the microorganisms is higher than 2 g/kg.

The cosurfactants are preferably selected as presenting a melting point lower than 0° C., and preferably lower than −20° C., and/or a solubility in water greater than 2 g for 100 g of water, and preferably greater than 10 g for 100 g of water, these two parameters are capable of study independently or simultaneously, according to the conditions of use of the microemulsions. It is easily understood that an expert in the field can be led to adjust the composition of the microemulsion according to whether it is a question of spraying on a polluted zone at sea or of treating soil to be rehabilitated, and according to temperature of use of these procedures.

The cosurfactants with the required characteristics for inclusion in the microemulsion according to the invention, alone or in a mixture, are selected from mono- and polyhydroxylated alcohols containing less than 10 carbon atoms, and their ether derivatives; mono- and polycarboxylic, acids or esters, possibly mono or polyhydroxylated and including $C_1$ to $C_7$ carbon length chains; straight-chain ketones including at least 5 carbon atoms, and lactones.

Suitable monoalcohols useful as cosurfactants of the invention include $C_2$ to $C_8$ alkanols, with $C_2$ to $C_4$ preferred.

Preferred polyalcohols are diols, especially substituted ethylene glycols or their oligomers, and their ether derivatives with 4 to 10 carbon atoms. In particular, the preferred ether derivatives include diethylene glycol butyl ether, ethylene glycol monoethyl ether, and ethylene glycol monomethyl ether.

Preferred monocarboxylic compounds, optionally hydroxylated, are carboxylic acids having 1 to 4 carbon atoms and their esters derived from $C_1$ to $C_5$ monoalcohols. Especially preferred monocarboxylic compounds are formic, acetic, butyric, and lactic acids, and their alkyl esters containing up to 6 carbon atoms the alkyl group, with n-butyl formate and ethyl lactate being preferred.

Preferred dicarboxylic compounds, optionally hydroxylated, are dicarboxylated acids containing from 3 to 6 carbon atoms and their esters from $C_1$ to $C_5$ monoalcohols. Especially preferred dicarboxylic compound are malonic and succinic acids and their esters, preferably dialkyl malonates, including diethyl malonate, and the dialkyl succinates, including dimethyl succinate.

Suitable preferred ketones of the invention include dialkyl detones containing, at most, 6 carbon atoms, especially methyl ethyl ketone.

The preferred lactone is γ-butyrolactone.

According to the present invention the preferred combinations of surfactants and cosurfactants are obtained by combining of an alkyl phosphoric ester, the alkyl radical containing, at most, 6 carbon atoms, and with, at most, three ethyoxylated groups with combinations of at least two cosurfactants.

In a first combination of surfactants a carboxylic acid is mixed with another carboxylic acid, optionally hydroxylated, esters thereof, mono and polyalcohols and ether derivatives thereof, ketones, and lactones. The preferred combinations are acetic acid/butanoic acid, acetic acid/ethyl lactate, acetic acid/ethanol, acetic acid/ethylene glycol butyl ether, acetic acid/methyl ethyl ketone, and acetic acid/γ-butyrolactone.

In a second combination of surfactants are at least one ether of ethylene glycol or its oligomers, preferably diethylene glycol butyl ether, is mixed with an alkanol, a ketone such as methyl ethyl ketone, or a monocarboxylic acid ester such as butyl formate.

In a third combination of surfactants are at least one ester of a dicarboxylic acid, such as alkyl succinates or alkyl malonates, is mixed with an alkanol or a ketone. The preferred combinations are dimethyl succinate/ethanol and dimethyl succinate/methyl ethyl ketone.

The nitrogenous compound component of the microemulsion is selected from amino acids, urea and its derivatives, while the organic phase is an animal or vegetable oil or a fatty acid, oleic acid being preferred.

Having generally described this invention, a further understanding can be obtained by reference to certain specific Examples which are provided herein for purposes of illustration only and are not intended to be limiting unless otherwise specified.

EXAMPLES

Example 1

The present example shows that, according to the surfactant/cosurfactant combinations available on the market, only the synergistic combinations of the invention allow the preparation of stable microemulsions at temperatures of −10° C. to +50° C., which are fluid at 5° C.

Compositions of Formulas A, B, and C are shown in Table 1 below. The amount of each component of a formula is percent by weight based on the weight of the emulsion.

TABLE I

| Components | Formula A | Formula B | Formula C |
|---|---|---|---|
| Surfactant | 23.7 | 23.4 | 22.4 |
| Cosurfactant | 10.8 | 12 | 16 |
| Water | 23.6 | 23.3 | 22.3 |
| Urea | 15.7 | 15.4 | 14.4 |
| Oleic acid | 26.2 | 25.9 | 24.9 |

In Table II below, the influence of the surfactant/cosurfactant pair is demonstrated by essentially varying the nature of the surfactant, that is by varying the length of the alkyl chain and the number of ethoxylated groups in the phosphoric ester. For that, six different surfactants are used which are characterized by the length of the C alkyl chain and by the number of ethoxylated groups (EO). In each sample, the amounts of alkyl phosphonic ester and cosurfactant conforms to the amounts of these surfactants in Formula A, B or C. The samples according to the invention are called $X_i$ and those given as comparative samples are called $T_i$.

TABLE II

| Sample | Formula | Surfactant | Cosurfactant | Temperature °C. +5 | 20 | 50 | Viscosity at 5° C. (mPa·s) |
|---|---|---|---|---|---|---|---|
| $T_1$ | A | $C_{12}$-$C_{14}$ 4EO | BEG | M | M | M | >1000 |
| $T_2$ | A | $C_{12}$-$C_{14}$ 4EO | BDG | M | M | M | >1000 |
| $T_3$ | C | $C_{12}$-$C_{14}$ 4EO | BDG | M | M | M | >1000 |
| $T_4$ | D | $C_{12}$-$C_{14}$ 4EO | Ethyl lactate | M | M | 2φ | >1000 |
| $X_1$ | C | $C_8$ 3EO | BDG | M | M | M | 156 |
| $X_2$ | C | $C_5$ 3EO | Ethyl lactate | M | M | M | 162 |
| $T_5$ | C | $C_{10}$-$C_{14}$ 4EO | BDG | M | M | M | >1000 |
| $T_6$ | C | $C_{10}$-$C_{14}$ 4EO | Ethyl lactate | M | M | M | >1000 |
| $T_7$ | C | $C_{12}$-$C_{14}$ 3EO | BDG | M | M | M | >1000 |
| $T_8$ | C | $C_{12}$-$C_{14}$ 3EO | Ethyl lactate | M | 2φ | M | >1000 |
| $T_9$ | C | $C_{13}$ 6EQ | BDG | M | M | M | >1000 |
| $T_{10}$ | C | $C_{13}$ 6EO | Ethyl lactate | M | 2φ | M | >1000 |
| $T_{11}$ | C | $C_{10}$-$C_{14}$ 10EO | BDG | M | M | M | >1000 |
| $T_{12}$ | C | $C_{10}$-$C_{14}$ 10EO | Ethyl lactate | M | 2φ | M | >1000 |
| $T_{13}$ | C | $C_{10}$-$C_{14}$ 6EO | BDG | M | M | M | >1000 |
| $T_{14}$ | C | $C_{10}$-$C_{14}$ 6EO | Ethyl lactate | M | 2φ | M | >1000 |
| $T_{15}$ | C | $C_{12}$-$C_{14}$ 4EO | BDG/Ethyl lactate 9.6/6.4 | M | M | M | >1000 |
| $T_{16}$ | C | $C_{12}$-$C_{14}$ 4EO | BDG/Ethyl lactate 8/8 | M | M | 2φ | >1000 |

BEG=ethylene glycol butyl ether
BDG=diethylene glycol butyl ether
(70/30 di/mono)
M=monophase
12φ=diphasic, oil phase in excess According to the results presented in the Table it is clear that surfactants with shorter chains (less than $C_{12}$) allow microemulsions to be obtained that are stable over a wide range of temperatures, especially at low temperatures, and at the same time have low viscosities at 5° C.

Example 2

This example shows the stability of microemulsions of the invention when an alkyl phosphoric ester with a chain length of less than 12, here 6, and number of ethoxylated groups less than 10, here 3, is used as surfactant, as in samples $X_1$ and $X_2$ described in Table II of Example 1, and when the nature of the cosurfactant(s) used is (are) varied.

As in Example 1, Table III shows the measured viscosity and stability values of emulsions for samples of the invention $X_i$ and comparative samples $T_j$.

TABLE III

| Sample | Formula | Cosurfactant | Temperatures in ° C. -7 | +5 | +20 | +50 | Viscosity mPa · sec at +5° C. |
|---|---|---|---|---|---|---|---|
| $X_1$ | C | BDG | M | M | M | M | 158 |
| $X_2$ | C | Ethyl lactate | M | M | M | M | 139 |
| $X_3$ | A | BDG | M | M | M | M | 158 |
| $X_4$ | A | Ethyl lactate | M | M | M | M | 178 |
| $X_5$ | B | BDG/Ethyl lactate 8/4 | M | M | M | M | 162 |
| $T_{17}$ | C | Lactic acid | M | M | M | M | >1000 |
| $X_6$ | B | Triethyl citrate | M | M | M | M | 178 |
| $X_7$ | B | Diethyl malonate | M | M | M | M | 128 |
| $T_{18}$ | B | Diethyl oxalate | M | M | M | 2φ | >1000 |
| $X_8$ | B | Dimethyl succinate | M | M | M | M | 146 |
| $X_9$ | B | Ethyl formate | M | M | M | M | 139 |
| $T_{19}$ | B | Propyl formate | 2φ | M | M | 2φ | 131 |
| $X_{10}$ | C | Isopropyl formate | M | M | M | M | 95 |
| $T_{20}$ | B | Butyl formate | 2φ | 2φ | 2φ | M | . |
| $T_{21}$ | B | Ethanol | 2φ | 2φ | M | 2φ | . |
| $T_{22}$ | B | Isopropanol | 2φ | 2φ | M | 2φ | . |
| $T_{23}$ | B | Isobutanol | 2φ | 2φ | M | 2φ | . |
| $X_{11}$ | B | Tert-butanol | M | M | M | M | . |
| $T_{24}$ | B | γ-Butyrolactone | M | M | M | M | >1000 |
| $T_{25}$ | B | MEG | 2φ | M | M | M | >1000 |
| $T_{26}$ | B | EEG | M | M | M | M | >1000 |
| $X_{12}$ | B | MEC | M | M | M | M | 131 |
| $X_{13}$ | B | Ethanoic acid | M | M | M | M | 162 |
| $X_{14}$ | B | Butanoic acid | M | M | M | M | 119 |
| $X_{15}$ | B | BDG/MEC 9.6/2.4 | M | M | M | M | 148 |
| $X_{16}$ | B | BDG/ethanol 9/3 | M | M | M | M | 106 |
| $X_{17}$ | B | BDG/butyl formate 9/3 | M | M | M | M | 131 |
| $X_{18}$ | B | BDG/acetic acid 6/6 | M | M | M | M | 151 |
| $X_{19}$ | B | Acetic acid/butanoic acid 6/6 | M | M | M | M | 147 |
| $X_{20}$ | B | Acetic acid/ethyl lactate 8/4 | M | M | M | M | 131 |
| $X_{21}$ | B | Acetic acid/ethanol 8/4 | M | M | M | M | 131 |
| $X_{22}$ | B | Acetic acid/γ-butyrolactone 8.5/3.5 | M | M | M | M | 200 |
| $X_{23}$ | B | Acetic acid/MEC 8/4 | M | M | M | M | 131 |
| $X_{24}$ | B | Dimethyl succinate/ethanol 8/4 | M | M | M | M | 140 |
| $X_{25}$ | B | Dimethyl succinate/MEC 8/4 | M | M | M | M | 122 |
| $T_{27}$ | B | MBC/γ-butyrolactone 4.25/7.8 | M | M | M | M | >1000 |

MEC = methyl ethyl ketone
EEG = ethylethylene glycol
MEG = monoethylene glycol

According to the results presented in the Table it is clear that only monophasic samples in the temperature range of -7° C. to +50° C., with viscosity at +5° C. of less than 200 mPa·sec allow the compositions to be fluid at low temperature, are considered as samples $X_i$. In addition, it will be noted that certain cosurfactants used alone in certain A, B, and C formulas cannot be considered as usable at low temperatures because of their excessive viscosity, but may be judged very worthwhile in combination with another cosurfactant according to the invention.

EXAMPLE 3

The present example shows the accelerator effect on the biodegradability of microemulsions of the invention, with regard to hydrocarbons with a radiorespirometry pilot.

The measurement is conducted with the aid of a laboratory apparatus called a radiorespirometer such as described by F. Bruchon, A. Basseres and J. C. Bertrand, Biotechnol. Lett. (1996), 18(1), 111–16. It enables continuous observation of the digestion of radioactive hydrocarbons, while evaluating the abiotic losses on each culture which avoids incubating with sterile cultures.

100 mL of a reaction medium is formulated from synthetic seawater, bacterial flora and phenanthrene labeled with $^{14}C$, biodegradable with difficulty, at 100 mg/L, in culture flasks or 250-mL erlenmeyers equipped with two lateral Torion [joints], with one being connected to the inlet for oxygen, and the other being connected to a trap for hydrocarbons formed by ORBO-43 columns sold by Supelco. The flow of oxygen for aeration is adjusted to 5 mL/min, and the medium is agitated with a back-and-forth agitator at 80 oscillations per minute. These reactors, thus agitated, are placed in the dark to incubate at 20° C. for one month. Evaporated hydrocarbons are absorbed on the hydrocarbon traps. The flow of air entrains $CO_2$ labeled with $^{14}C$ derived from digestion of the phenanthrene into a $CO_2$ trap formed by a solution of 4N sodium hydroxide.

During this incubation for 1 month, in order to measure the kinetics of digestion, samples are taken every two or three days, depending on the results obtained. Three aliquot samples of 0.5 mL of the solution of 4N sodium hydroxide are placed for measurement in 10 mL of Hionic-Fluor Cocktail from Packard.

The bacterial flora used to test the effectiveness of the microemulsions, or rather of the surfactant/cosurfactant pair, is a complex natural flora of marine origin. Before starting the tests, this flora is reactivated by being kept at 80° C. on rich medium Marine Agar 2216 from Difco for eight hours. Then it is precultured on synthetic seawater of the Instant Ocean type at 33 g/L and enriched with 50 mg/L of light crude Arab oil for two days in the presence of nitrogenous and phosphorous nutrients, ammonium chloride, and potassium hydrogen phosphate, in concentrations such that the ratios C/N/P are equal to 106/16/1.

The labeled phenanthrene used is 9-$^{14}C$ phenanthrene, Sigma product 31,528-1.

The tests are carried out in 9 reactors placed in series, all containing the same reaction medium formed from synthetic sea water, labeled phenanthrene at 100 g/L, activated bacterial flora at 10% v/v, and a neutral pH buffer, TRIS at 6 g/L, these concentrations being reported as the reaction medium. Various microemulsions of the invention and of the prior art are introduced into 8 of these reactors. The concentrations of the microemulsions in the reaction media at the beginning of the trials are 10 mg/L. These microemulsions correspond to microemulsions described in Examples 1 and 2. The details of the content of each reactor are given below.

Reactor 1: reaction medium alone=control
Reactor 2: reaction medium+$X_{15}$
Reactor 3: reaction medium+$X_{16}$
Reactor 4: reaction medium+$X_{18}$
Reactor 5: reaction medium+$X_{19}$
Reactor 6: reaction medium+$X_{20}$
Reactor 7: reaction medium+$X_{23}$
Reactor 8: reaction medium+$X_5$
Reactor 9: reaction medium+$T_1$ The results, backed up by figures and expressed in %, of the levels of digestion of the phenanthrene in the presence of these different microemulsions are shown in Table IV below.

TABLE IV

| Digestion level | Control | $X_{15}$ | $X_{16}$ | $X_{18}$ | $X_{19}$ | $X_{20}$ | $X_{23}$ | $X_5$ | $T_1$ |
|---|---|---|---|---|---|---|---|---|---|
| 0 | 0 | 0 | 0 | 0 | 0 | 0 | 0 | 0 | 0 |
| 8 days | 5 | 0.1 | 0.8 | 0.1 | 1.6 | 2.19 | 1.3 | 0.05 | 5 |
| 14 days | 12.9 | 4.1 | 43.7 | 1.6 | 1.5 | 51.2 | 9.4 | 2.8 | 29.1 |
| 20 days | 18 | 24.8 | 68.4 | 1.8 | 1.5 | 71 | 44.2 | 34.1 | 42 |
| 25 days | 22.6 | 55 | 76.4 | 12.7 | 1.6 | 78.2 | 56.8 | 56.4 | 51.9 |

A better digestion of the phenanthrene is noted in the presence of microemulsions $X_{16}$ and $X_{20}$. For certain other formulations of the invention, a certain latent period is observed before digestion is produced.

Microemulsions $X_{18}$ and $X_{19}$ are less favorable because they are more biodegradable than phenanthrene, by the bacteria; they are biodegraded before phenanthrene.

The disclosure of French priority Application Number 9908678 filed Jul. 6, 1999 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A microemulsion, comprising:
   a mixture of (1) nitrogenous compounds, (2) from 10–35% by weight of an alkyl or alkenyl phosphoric ester surfactant, the alkyl and alkenyl groups of which contain less than 12 carbon atoms per group and the ester surfactant containing from 1 to 10 alkoxy radicals, (3) from 3 to 20% by weight of at least one cosurfactant and (4) a vegetable oil, an animal oil or a fatty acid and (5) a plasticizer, said microemulsion having a viscosity at 5° C. less than or equal to 200 mPa·sec and is stable at a temperature of −10° C. to +50° C.

2. The microemulsion according to claim 1, wherein the at least one cosurfactant has an oral toxicity in rats such that the lethal dose for 50% of the rats is higher than 2 g/kg.

3. The microemulsion according to claim 1, wherein the at least one cosurfactant has a melting point lower than 0° C. and/or a solubility in water higher than 2 g in 100 g of water.

4. The microemulsion according to claim 1, wherein the at least one cosurfactant, alone or in a mixture, is selected from the group consisting of (1) mono and polyhydroxylated alcohols containing less than 10 carbon atoms and their ether derivatives, (2) mono- and polycarboxylic compounds, acids, or esters, and (3) mono or polyhydroxylated, $C_1$ to $C_7$-straight chain ketones and cyclic ketones containing at least 5 carbon atoms, and (4) lactones.

5. The microemulsion according to claim 4, wherein the monoalcohols are $C_2$ to $C_8$ alkanols.

6. The microemulsion according to claim 1, wherein the at least one cosurfactant is polyalcohols comprising diols and their ether derivatives having 4 to 10 carbon atoms.

7. The microemulsion according to claim 6, wherein the ether derivatives comprise ethylene glycol and its oligomers and are further selected from the group consisting of diethylene glycol butyl ether, ethylene glycol, monoethyl ether, and ethylene glycol diethyl ether.

8. The microemulsion according to claim 4, wherein the monocarboxylic compound is a monocarboxylic acid of 1 to 4 carbon atoms, and esters thereof prepared from $C_1$ to $C_5$ monoalcohols.

9. The microemulsion according to claim 8, wherein the monocarboxylic compound is selected from the group consisting of formic, acetic, butyric, and lactic acids and their $C_1$ to $C_6$ alkyl esters.

10. The microemulsion according to claim 4, wherein the polycarboxylic compounds are dicarboxylic compounds and are further selected from the group consisting of dicarboxylic acids containing 3 to 6 carbon atoms, and esters thereof prepared from $C_1$ to $C_5$ monoalcohols.

11. The microemulsion according to claim 10, wherein the dicarboxylic compounds are selected from the group consisting of malonic acid, succinic acid, dialkyl malonate, and dialkyl succinates.

12. The microemulsion according to claim 4, wherein the straight chain ketones are di-$C_1$ to $C_6$-alkyl ketones.

13. The microemulsion according to claim 4, wherein the lactones comprise a lactone containing up to 6 carbon atoms.

14. The microemulsion according to claim 1, wherein the phosphoric ester surfactant is an alkyl phosphoric ester whose alkyl radical contain at most 6 carbon atoms and which contains no more than three ethoxy groups and said cosurfactant is at least two cosurfactants.

15. The microemulsion according to claim 1, wherein the at least one cosurfactant is (1) a mixture of a carboxylic acid and at least one other carboxylic acid, optionally hydroxylated, and their esters thereof, (2) mono- or polyalcohols and their ether derivatives, (3) ketones or (4) lactones.

16. The microemulsion according to claim 14, wherein the at least two cosurfactants are selected from the combinations of acetic acid-butanoic acid, acetic acid-ethyl lactate, acetic acidethanol, acetic acid-diethylene glycol butyl ether, acetic acid-methyl ethyl ketone and acetic acid-γ-butyrolactone.

17. The microemulsion according to claim 1, wherein the at least one cosurfactant is a mixture and is obtained by mixing at least one ether of ethylene glycol or its oligomers with an alkanol, a ketone, or a monocarboxylic acid ester.

18. The microemulsion according to claim 1, wherein the at least one cosurfactant is a mixture and is obtained by mixing at least one ester of a dicarboxylic acid with an alkanol or a ketone.

19. The microemulsion according to claim 18, wherein the at least one cosurfactant is selected from the group consisting of dimethyl succinate-ethanol and dimethyl succinate-methyl ethyl ketone.

* * * * *

UNITED STATES PATENT AND TRADEMARK OFFICE
CERTIFICATE OF CORRECTION

PATENT NO. : 6,190,646 B1
DATED : February 20, 2001
INVENTOR(S) : Tellier et al.

It is certified that error appears in the above-identified patent and that said Letters Patent is hereby corrected as shown below:

<u>Title page, Item [54] and Column 1, lines 1-3,</u>
Title, should be: -- MICROEMULSION USEFUL AS A BIODEGRADATION ACCELERATOR --

Signed and Sealed this

Twenty-sixth Day of July, 2005

JON W. DUDAS
*Director of the United States Patent and Trademark Office*